United States Patent [19]
Khouri

[11] Patent Number: 5,171,866
[45] Date of Patent: Dec. 15, 1992

[54] ETHYLENICALLY UNSATURATED CYCLIC ORTHO ESTERS

[75] Inventor: Farid F. Khouri, Clifton Park, N.Y.

[73] Assignee: General Electric Company, Schenectady, N.Y.

[21] Appl. No.: 645,179

[22] Filed: Jan. 24, 1991

[51] Int. Cl.$^5$ ............................................. C07D 317/24
[52] U.S. Cl. .................................... 548/449; 549/372; 549/347
[58] Field of Search ............... 549/449, 374, 375, 372, 549/347

[56] References Cited

U.S. PATENT DOCUMENTS

| | | | |
|---|---|---|---|
| 2,877,215 | 3/1959 | Fahg | 549/454 |
| 3,518,226 | 6/1970 | Wood | 524/378 |
| 4,076,727 | 2/1978 | Zey et al. | 549/454 |

OTHER PUBLICATIONS

Endo et al. J. Poly. Sci.: Part C, 26,517–520 (1988).
Endo et al., Polymer, J., 14,485–488 (1982).

*Primary Examiner*—Jane T. Fan
*Attorney, Agent, or Firm*—William H. Pittman

[57] ABSTRACT

Ethylenically unsaturated cyclic ortho esters are prepared by the reaction of a hydroxy-substituted cyclic ortho ester such as 4-hydroxymethyl-2-methoxy-2-methyl-1,3-dioxolane with acryloyl chloride, methacryolyl chloride, vinylbenzyl chloride or the like. They form polymers, especially EPDM graft copolymers, which are useful in the formation of copolymer-containing compositions with polyesters, polyamides and the like. The copolymer-containing compositions have excellent physical properties and may be employed to compatibilize blends of the same polymers.

20 Claims, No Drawings

ETHYLENICALLY UNSATURATED CYCLIC ORTHO ESTERS

This invention relates to new ethylenically unsaturated monomers, and more particularly to monomers containing cyclic ortho ester functionality.

In recent years, there has been considerable interest in developing polymer compositions which include normally incompatible polymers. Examples are compositions comprising linear polyesters such as poly(ethylene terephthalate) and poly(butylene terephthalate) in combination with olefin and olefin-diene polymers.

It might be expected that various properties of the linear polyesters, such as tensile strength, tensile elongation and impact strength, would be improved by the addition of olefin or olefin-diene polymers. However, the resulting blends exhibit incompatibility as evidenced by gross phase separation and frequently degradation, rather than improvement, of physical properties.

One method of compatibilizing otherwise incompatible polymer blends is to incorporate therein a copolymer, typically a block copolymer, of the otherwise incompatible polymers. Copolymers of this type can be formed by incorporating in one polymer structural units which are chemically reactive with the other polymer.

Thus, for example, linear polyesters or polyamides having terminal carboxylic acid groups can undergo reaction with olefin or olefin-diene copolymers containing epoxy groups, either as substituents on the polymer chain or as grafted units. Reference is made, for example, to U.S. Pat. No. 4,965,111. Similarly, amine-terminated polyamides can undergo reaction with olefin or olefin-diene polymers containing integral or grafted maleic anhydride moieties. The resulting block copolymers do not exhibit the indicia of incompatibility which are found in simple blends. Moreover, they are often useful as compatibilizers for blends of the otherwise incompatible forms of the two polymers.

While polymers containing reactive substituents or grafted units such as epoxy and anhydride groups are known, many of them have not met with wide commercial acceptance. One possible reason is the relative chemical inactivity of such polymers, whereupon it is difficult to promote the copolymer-forming reaction to any substantial extent.

The present invention provides a series of ethylenically unsaturated monomers which may be employed in the preparation of a wide variety of polymers, particularly copolymers. These monomers contain highly reactive cyclic ortho ester groups as substituents, which remain in the polymers prepared therefrom. Said cyclic ortho ester groups can undergo reaction with numerous other polymers, forming copolymer-containing compositions with excellent properties.

Accordingly, the invention includes ethylenically unsaturated cyclic ortho esters having the formula

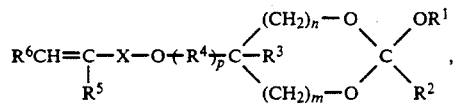

wherein:
each of $R^1$ and $R^2$ is $C_{1-10}$ primary or secondary alkyl or aralkyl or a $C_{6-10}$ aromatic radical;
$R^3$ is hydrogen or $C_{1-4}$ primary or secondary alkyl;
$R^4$ is an unsubstituted or substituted $C_{1-6}$ alkylene or $C_{6-10}$ arylene radical;
$R^5$ is hydrogen or methyl;
$R^6$ is hydrogen, $C_{1-6}$ alkyl or a $C_{6-10}$ aromatic radical;
X is a substantially inert linking group;
m is 0 or 1;
n is from 1 to 2-m; and
p is 0 or 1.

An essential feature of the compounds of this invention is the presence of a cyclic ortho ester moiety. The $R^1$ value therein may be a $C_{1-10}$ primary or secondary alkyl radical such as methyl, ethyl, n-propyl, isopropyl, n-butyl, isobutyl, secondary butyl, n-hexyl, isooctyl or n-decyl, or a corresponding aralkyl radical. Most often, it is $C_{1-4}$ alkyl. Primary radicals and especially the methyl radical are generally preferred.

The $R^2$ value may be a $C_{1-4}$ primary or secondary alkyl radical as defined above for $R^1$, or a $C_{6-10}$ unsubstituted or substituted aromatic (preferably aromatic hydrocarbon) radical. Any substituents should be non-reactive under the conditions of the invention; examples are halo, nitro and alkoxy.

The $R^3$ radical may be hydrogen or an alkyl radical similar to $R^1$ and $R^2$. It is preferably hydrogen.

The $R^4$ radical is an unsubstituted or substituted $C_{1-6}$ alkylene radical, any substituents being inert to ortho ester formation and reaction with aryl chlorides; e.g., alkoxy. Preferably, $R^4$ is methylene.

The $R^6$ radical may be hydrogen, alkyl or aryl as previously defined. It is preferably hydrogen.

The X value may be any linking group which is substantially inert under the conditions of formation and polymerization of the cyclic ortho esters of the invention and copolymer formation from polymers thereof. Those skilled in the art will understand that a wide variety of groups fit this description, and the invention is not limited in that respect.

Suitable X groups include unsubstituted and substituted divalent aliphatic, alicyclic and aromatic radicals and combinations thereof, any substituents being of the type previously described. Said radicals may be attached to other divalent radicals such as carbonyl, sulfone, carbamoyl, disubstituted silicon and alkyl- and arylphosphoryl. The preferred X groups have the formulas

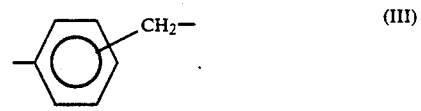

The cyclic ortho esters of this invention include acrylic and methacrylic acid esters, wherein X has formula II, as well as vinylbenzyl ethers, wherein X has formula III. Both vinyl ($R^5$ is hydrogen) and isopropenyl ($R^5$ is methyl) compounds are included; for example, acrylic and methacrylic acid esters. For the most part, $R^5$ is preferably hydrogen when X has formula III.

The values of m and n depend on whether the cyclic ortho ester moiety is a 5-membered or 6-membered ring. In general, 5-membered rings are preferred; that is, m is 0 and n is 1. However, the invention also includes compositions in which a 6-membered ring is present, which requires either than m and n both be 1 or that m be 0 and n be 2.

Also included are compounds in which p is 0; that is, compounds not containing an $R^4$ value. Most often, p will be 0 when the ortho ester ring is a 6-membered ring.

The ethylenically unsaturated cyclic ortho esters of this invention may be prepared by the reaction of a hydroxy-substituted ortho ester of the formula

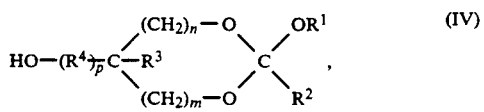

wherein $R^{1-4}$, m, n and p are as previously defined, with a suitable reagent such as acryloyl chloride, methacryloyl chloride or a vinylbenzyl chloride. Said reaction takes place under conventional conditions. In the case of acryloyl chloride or methacryloyl chloride, it typically occurs in the presence of a tertiary amine as acid acceptor and in solution in a relatively non-polar organic solvent. The hydroxy-substituted ortho ester and acryloyl or methyacryloyl chloride may be employed in approximately equimolar amounts, or the chloride may be employed in slight excess. The amine is generally present in excess, to ensure neutralization of all the acidic by-product formed.

Reaction between the hydroxy-substituted ortho ester and vinylbenzyl chloride is also conducted under conventional conditions, typically in the presence of an alkaline reagent such as sodium hydroxide. Again, the hydroxy-substituted ortho ester and vinylbenzyl chloride may be employed in roughly equimolar amounts, or, in this case, an excess of the ortho ester may be employed. The molar proportion of base is generally about equal to that of ortho ester. No solvent is generally necessary, although one may be employed if desired.

The preparation of the ortho esters of this invention is illustrated by the following examples. Molecular structures of all products in Examples 1-4 were confirmed by proton and carbon-13 nuclear magnetic resonance spectroscopy.

EXAMPLE 1

A 5-liter 3-necked flask fitted with a mechanical stirrer, pressure equalizing addition funnel and nitrogen inlet was charged with 301 grams (2.03 moles) of 4-hydroxymethyl-2-methoxy-2-methyl-1,3-dioxolane, 514 grams (5.08 moles) of triethylamine and 2 liters of methylene chloride. The flask was immersed in an ice-water bath and 193.1 grams (2.13 moles) of acryloyl chloride was added over 50 minutes under nitrogen, with stirring. The mixture was stirred at room temperature overnight and the filtrate was washed twice with 2-liter portions of water, dried over magnesium sulfate, filtered and vacuum stripped. A free radical inhibitor, 3-t-butyl-4-hydroxy-5-methylphenyl sulfide, was added in the amount of 200 ppm. to the residue which was then distilled under vacuum. The desired 4-acryloyloxymethyl-2-methoxy-2-methyl-1,3-dioxolane distilled at 80°-85° C./0.5-1.0 torr.

EXAMPLE 2

The procedure of Example 1 was repeated, employing 281 grams (1.9 moles) of 4-hydroxymethyl-2-methoxy-2-methyl-1,3-dioxolane, 481 grams (4.76 moles) of triethylamine and 199 grams (1.9 moles) of methacryloyl chloride. The product, 4-methacryloxymethyl-2-methoxy-2-methyl-1,3-dioxolane, was collected at 80° C./0.4 torr.

EXAMPLE 3

The procedure of Example 1 was repeated, employing 1 grams (100 mmol.) of 4-hydroxymethyl-2-methoxy-2-phenyl-1,3-dioxolane, 25.3 grams (250 mmol.) of triethylamine, 9.5 grams (105 mmol.) of acryloyl chloride and 150 ml. of methylene chloride. The crude product was purified by column chromatography over basic alumina, using 15% (by volume) ethyl acetate in hexane as an eluant, to yield the desired 4-acryloyloxymethyl-2-methoxy-2-phenyl-1,3-dioxolane.

EXAMPLE 4

A 4-necked 250-ml. round-bottomed flask equipped with a mechanical stirrer, a pressure equalizing addition funnel, a condenser and a thermometer was charged with 51.9 grams (350 ml.) of 4-hydroxymethyl-2-methoxy-2-methyl-1,3-dioxolane and 14.01 grams (350 mmol.) of powdered sodium hydroxide. The slurry was stirred for 15 minutes under nitrogen, after which 41.1 grams (270 mmol.) of vinylbenzyl chloride (isomeric mixture) was added dropwise over 10 minutes. The mixture was heated to 80° C., whereupon an exothermic reaction took place which caused the temperature to rise to 140° C. The mixture was stirred overnight under nitrogen, diluted with 400 ml. of methylene chloride and 5 ml. of triethylamine and washed twice with 250 ml. of aqueous sodium chloride solution. The organic layer was dried over magnesium sulfate, filtered and vacuum stripped, and the residue was purified by column chromatography over basic alumina using a 2:1 (by volume) mixture of hexane and methylene chloride as eluant. There was obtained the desired isomeric mixture of 4-(2-methoxy-2-methyl-1,3-dioxolanyl)methyl vinylbenzyl ethers.

The ethylenically unsaturated ortho esters of this invention may be polymerized under free radical conditions, either alone or in the presence of other monomers. The term "polymer", as used herein, includes addition homopolymers and, especially, copolymers with one or more other monomers. Such polymers are disclosed and claimed in copending, commonly owned application Ser. No. 07/716,157.

Polymerization by the free radical method may be effected in bulk, solution, suspension or emulsion, by contacting the monomer or monomers with a polymerization initiator either in the absence or presence of a diluent at a temperature of about 0°-200° C. Suitable initiators include benzoyl peroxide, hydrogen peroxide, azobisisobutyronitrile, persulfate-bisulfite, persulfate-sodium formaldehyde sulfoxylate, chlorate-sulfite and the like. Alternatively, polymerization may be effected by irradiation techniques, as by ultraviolet, electron beam or plasma irradiation.

A large variety of polymerizable compounds can be used to form copolymers with the ortho esters of this invention. They include the following:

(1) Unsaturated alcohols and esters thereof: Allyl, methallyl, crotyl, 1-chloroallyl, 2-chloroallyl, cinnamyl, vinyl, methylvinyl, 1-phenallyl and butenyl alcohols and esters of such alcohols with saturated acids such as acetic, phenylacetic, propionic, butyric, valeric, caproic and stearic; with unsaturated acids such as acrylic, α- substituted acrylic (including alkylacrylic, e.g., methacrylic, ethylacrylic, propylacrylic, etc. and arylacrylic such as phenylacrylic), crotonic, oleic, linolenic and linolenic; with polybasic acids such as oxalic, malonic, succinic, glutaric, adipic, pimelic, suberic, azelaic and sebacic; with unsaturated polybasic acids such as maleic, fumaric, citraconic, mesaconic, itaconic, methylenemalonic, acetylenedicarobxylic and aconitic; and with aromatic acids, e.g., benzoic, phthalic, terephthalic and benzoylphthalic acids.

(2) Unsaturated acids (examples of which appear above) and esters thereof with lower saturated alcohols, such as methyl, ethyl, propyl, isopropyl, butyl, isobutyl, secbutyl, tert-butyl, 2-ethylhexyl and cyclohexyl alcohols and with saturated lower polyhydric alcohols such as ethylene glycol, propylene glycol, tetramethylene glycol, neopentyl glycol and trimethylopropane.

(3) Unsaturated lower polyhydric alcohols, e.g., butenediol, and esters thereof with saturated and unsaturated aliphatic and aromatic, monobasic and polybasic acids, examples of which appear above.

(4) Esters of the above-described unsaturated acids, especially acrylic and methacrylic acids, with higher molecular weight monohydroxy and polyhydroxy materials such as decyl alcohol, isodecyl alochol, oleyl alcohol, stearyl alcohol, epoxy resins and polybutadiene-derived polyols.

(5) Vinyl cyclic compounds including styrene, o-, m-, p-chlorostyrenes, bromostyrenes, fluorostyrenes, methylstyrenes, ethylstyrenes and cyanostyrenes; di-, tri- and tetrachlorostyrenes, bromostyrenes, fluorostyrenes, methylstyrenes, ethylstyrenes, cyanostyrenes; vinylnaphthalene, vinylcyclohexane, divinylbenzene, trivinylbenzene, allylbenzene and heterocycles such as vinylfuran, vinylpridine, vinylbenzofuran, N-vinyl carbazole, N-vinylpyrrolidone and N-vinyloxazolidone.

(6) Unsaturated ethers such as methyl vinyl ether, ethyl vinyl ether, cyclohexyl vinyl ether, octyl vinyl ether, diallyl ether, ethyl methallyl ether and allyl ethyl ether.

(7) Unsaturated ketones, e.g., methyl vinyl ketone and ethyl vinyl ketone.

(8) Unsaturated amides, such as acrylamide, methacrylamide, N-phenylacrylamide, N-allylacrylamide, N-methylolacrylamide, N-allylcaprolactam and diacetone acrylamide.

(9) Unsaturated aliphatic hydrocarbons, for instance, ethylene, propylene, butenes, butadiene, isoprene, 2-chlorobutadiene and α-olefins in general.

(10) Unsaturated alkyl halides, e.g., vinyl fluoride, vinyl chloride, vinyl bromide, vinylidene chloride, vinylidene bromide, allyl chloride and allyl bromide.

(11) Unsaturated acid anhydrides, e.g., maleic, citraconic, itaconic, bis-4-cyclohexane-1,2-dicarboxylic and bicyclo(2.2.1.)-5-heptene-2,3-dicarboxylic anhydrides.

(12) Unsaturated nitriles, e.g., acrylonitrile, methacrylonitrile and other substituted acrylonitriles.

While ordinary random addition polymers may be prepared, the preferred polymers are graft copolymers prepared by grafting the ortho esters of this invention on previously formed polymers. More preferably, said previously formed polymers are copolymers comprising ethylene and propylene structural units; and still more preferably, copolymers also containing structural units derived from non-conjugated dienes, said copolymers frequently being identified hereinafter as "EPDM copolymers". Such graft copolymers may be conveniently prepared by absorption of the ethylenically unsaturated ortho ester and a free radical polymerization catalyst on the EPDM copolymer followed by grafting, frequently effected by extrusion at a temperatures in the range of about 150°-300° C.

The preparation of graft copolymers of the ortho esters of this invention is illustrated by the following examples.

EXAMPLES 5-9

Mixtures of the ortho esters of this invention and 1 gram of 2,5-dimethyl-2,5-di(t-butylperoxy)hexane were premixed and combined with 1 kilogram of a commercially available EPDM copolymer containing about 83 mole percent ethylene and about 5.4 mole percent norbornene units. The blends were stored for about 16 hours at 20.C to enable the ortho ester and polymerization initiator to be completely absorbed by the EPDM pellets, and were then extruded on a twin-screw extruder with zone set temperatures ranging from 120° to 205° C. The extrudates were cooled in a water bath, pelletized and dried in vacuum.

The proportion of the ethylenically unsaturated ortho ester grafted on the EPDM copolymer was determined by dissolving a sample of the graft copolymer in xylene at about 130° C., pouring the resulting solution into acetone and filtering and drying the purified copolymer, which was then analyzed by Fourier transform infrared spectroscopy. Gel content was determined by continuous extraction with hot xylene for 48 hours followed by drying and weighing of the insoluble residue. The results are given in Table I, with all percentages being by weight.

TABLE I

| Ortho ester: | Example | | | | |
|---|---|---|---|---|---|
| | 5 | 6 | 7 | 8 | 9 |
| Example | 1 | 1 | 1 | 2 | 3 |
| Percent based on EPDM copolymer | 0.3 | 1.0 | 3.0 | 1.0 | 1.3 |
| Amount grafted, % | >90 | >90 | >90 | 50 | — |
| Gel, % | 0 | 40 | 40 | 0 | — |

The ortho ester polymers react with other polymers containing reactive groups, particularly those capable of nucleophilic substitution such as amine, hydroxy, thio and carboxy groups and functional derivatives thereof, to form copolymer-containing compositions. Included are copolymer-containing compositions with polymers otherwise incompatible with EPDM copolymers, including linear polyesters and polyamides. Such copolymer-containing compositions and the method for their preparation are disclosed and claimed in copending, commonly owned application Ser. No. 07/645,180.

By reason of the presence of the copolymer, said compositions are compatible and may be molded into articles having excellent physical properties. They are also useful for further compatibilizing blends of the two polymers to form molding compositions having similar excellent properties.

Polyesters suitable for preparing copolymer-containing compositions include those comprising structural units of the formula

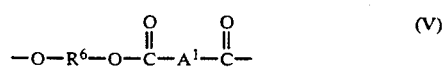

wherein each $R^6$ is independently a divalent aliphatic, alicyclic or aromatic hydrocarbon or polyoxyalkylene radical and $A^1$ is a divalent aromatic radical. Such polyesters include thermoplastic polyesters illustrated by poly(alkylene dicarboxylates), elastomeric polyesters, polyarylates, and polyester copolymers such as copolyestercarbonates. Because the principal reaction which occurs with the ortho ester groups involves a carboxylic acid group of the polyester, it is highly preferred that said polyester have a relatively high carboxylic end group concentration. Concentrations in the range of about 5-250 microequivalents per gram are generally suitable, with 20-150 microequivalents per gram being preferable and 20-80 being particularly desirable.

The polyester may include structural units of the formula

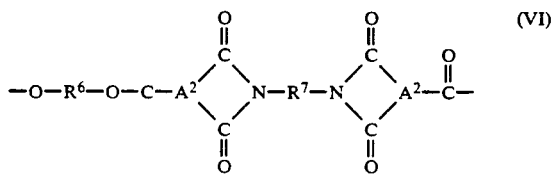

wherein $R^6$ is as previously defined, $R^7$ is a polyoxyalkylene radical and A2 is a trivalent aromatic radical. The $A^1$ radical in formula V is most often p- or m-phenylene or a mixture thereof, and $A^2$ in formula VI is usually derived from trimellitic acid and has the structure

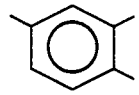

The $R^6$ radical may be, for example, a $C_{2-10}$ alkylene radical, a $C_{6-10}$ alicyclic radical, a $C_{6-20}$ aromatic radical or a polyoxyalkylene radical in which the alkylene groups contain about 2-6 and most often 4 carbon atoms. As previously noted, this class of polyesters includes the poly(alkylene terephthalates) and the polyarylates. Poly(alkylene terephthalates) are frequently preferred, with poly(ethylene terephthalate) and poly(butylene terephthalate) being most preferred.

The preferred polyesters are poly(ethylene terephthalate) and poly(butylene terephthalate), generally having a number average molecular weight in the range of about 20,000-70,000, as determined by intrinsic viscosity (IV) at 30° C. in a mixture of 60% (by weight) phenol and 40% 1,1,2,2-tetrachloroethane.

Polyamides may also be employed for the formation of copolymer-containing compositions. Included are those prepared by the polymerization of a monoaminomonocarboxylic acid or a lactam thereof having at least 2 carbon atoms between the amino and carboxylic acid group, of substantially equimolar proportions of a diamine which contains at least 2 carbon atoms between the amino groups and a dicarboxylic acid, or of a monoaminocarboxylic acid or a lactam thereof as defined above together with substantially equimolar proportions of a diamine and a dicarboxylic acid. (The term "substantially equimolar" proportions includes both strictly equimolar proportions and slight departures therefrom which are involved in conventional techniques for stabilizing the viscosity of the resultant polyamides.) The dicarboxylic acid may be used in the form of a functional derivative thereof, for example, an ester or acid chloride.

Examples of the aforementioned monoaminomonocarboxylic acids or lactams thereof which are useful in preparing the polyamides include those compounds containing from 2 to 16 carbon atoms between the amino and carboxylic acid groups, said carbon atoms forming a ring containing the —CO—NH— group in the case of a lactam. As particular examples of aminocarboxylic acids and lactams there may be mentioned ε-aminocaproic acid, butyrolactam, pivalolactam, ε-caprolactam, capryllactam, enantholactam, undecanolactam, dodecanolactam and 3- and 4-aminobenzoic acids.

Diamines suitable for use in the preparation of the polyamides include the straight chain and branched chain alkyl, aryl and alkaryl diamines. Illustrative diamines are trimethylenediamine, tetramethylenediamine, pentamethylenediamine, octamethylenediamine, hexamethylenediamine (which is often preferred), trimethylhexamethylenediamine, m-phenylenediamine and mxylylenediamine.

The dicarboxylic acids may be represented by the formula

HOOC—Y—COOH wherein Y is a divalent aliphatic or aromatic group containing at least 2 carbon atoms. Examples of aliphatic acids are sebacic acid, octadecanedioic acid, suberic acid, glutaric acid, pimelic acid and adipic acid.

Both crystalline and amorphous polyamides may be employed, with the crystalline species often being preferred by reason of their solvent resistance. Typical examples of the polyamides or nylons, as these are often called, include, for example, polyamide-6 (polycaprolactam), 66 (polyhexamethylene adipamide), 11, 12, 63, 64, 6/10 and 6/12 as well as polyamides from terephthalic acid and/or isophthalic acid and trimethylhexamethylenediamine; from adipic acid and m-xylylenediamines; from adipic acid, azelaic acid and 2,2-bis(p-aminophenyl)propane or 2,2-bis-(p-aminocyclohexyl)propane and from terephthalic acid and 4,4'-diaminodicyclohexylmethane. Mixtures and/or copolymers of two or more of the foregoing polyamides or prepolymers thereof, respectively, are also within the scope of the present invention. Preferred polyamides are polyamide-6, 46, 66, 11 and 12, most preferably polyamide-66.

For the preparation of copolymer-containing compositions, a blending method which results in the formation of an intimate blend is preferred. Suitable procedures include solution blending, although such procedures are of limited applicability to many polyesters and polyamides by reason of their insolubility in most common solvents. For this reason and because of the availability of melt blending equipment in commercial polymer processing facilities, melt reaction procedures are generally preferred. Conventional melt blending procedures and equipment may be employed, with extrusion often preferred because of its relative convenience and particular suitability. Typical reaction temperatures are in the range of about 175°-350° C.

Those skilled in the art will be familiar with blending methods and apparatus capable of intimately blending resinous constituents, especially by kneading. They are exemplified by disc-pack processors and various types of extrusion equipment. Illustrations of the latter are continuous mixers; single screw kneading extruders; counterrotating, non-intermeshing twin screw extruders having screws which include forward-flighted compounders, cylindrical bushings and/or left-handed screw elements; corotating, intermeshing twin screw extruders; and extruders having screws which include at least one and preferably at least two sections of kneading block elements.

In addition to copolymer, the copolymer-containing compositions may also contain unreacted polyester, polyamide or the like. In any event, molded parts produced from said compositions are generally ductile and have higher impact strengths, tensile strengths and/or tensile elongations than those produced from simple blends, which are incompatible and often exhibit brittleness or delamination.

There may also be present in the copolymer-containing compositions conventional ingredients such as fillers, flame retardants, pigments, dyes, stabilizers, antistatic agents, crystallization aids, mold release agents and the like, as well as resinous components not previously discussed including auxiliary impact modifying polymers.

The proportions of ortho ester polymer, other polymer and other resinous materials are not critical; they may be widely varied to provide compositions having the desired properties. Most often, the ortho ester polymer is employed in an amount in the range of about 5–95%, preferably about 5–65%, of the composition by weight.

The preparation of copolymer-containing compositions from ortho ester polymers is illustrated by the following examples. All percentages are by weight.

EXAMPLES 10–17

Dry blends comprising ortho ester-grafted EPDM copolymers and poly(butylene terephthalate) were prepared and extruded at temperatures in the range of 250.C. The extrudates were the desired copolymer-containing compositions; they were pelletized, dried and molded into test specimens which were tested for tensile strength and elongation (ASTM procedure D638) and notched Izod impact strength (ASTM procedure D256).

The results are given in Tables II and III, in comparison with five controls employing (A-D) a blend prepared from unfunctionalized EPDM copolymer, and (E) a blend prepared from EPDM copolymer similarly grafted with 3% glycidyl methacrylate.

TABLE II

|  | Example | | | Control | Control |
|---|---|---|---|---|---|
|  | 10 | 11 | 12 | A | E |
| Polyester, parts | 50 | 50 | 50 | 50 | 50 |
| Ortho ester-grafted EPDM: | | | | | |
| Example | 5 | 6 | 8 | — | — |
| Parts | 50 | 50 | 50 | 50 | 50 |
| Tensile strength, MPa. | 16.9 | 24.2 | 17.3 | 13.9 | 18.5 |
| Tensile elongation, % | 240 | 370 | 290 | 65 | 230 |

TABLE III

|  | Example | | | | | Control | | |
|---|---|---|---|---|---|---|---|---|
|  | 13 | 14 | 15 | 16 | 17 | B | C | D |
| Polyester, parts | 95 | 90 | 80 | 95 | 90 | 95 | 90 | 80 |
| Ortho ester-grafted EPDM: | | | | | | | | |
| Example | 6 | 6 | 6 | 9 | 9 | — | — | — |
| Parts | 5 | 10 | 20 | 5 | 10 | 5 | 10 | 20 |
| Impact strength, joules/m. | 64 | 641 | 849 | 264 | 844 | 27 | 32 | 53 |

From Table II, it is apparent that copolymer-containing compositions prepared from EPDM copolymers grafted with the ortho esters of this invention have substantially higher tensile strengths and tensile elongations than the control employing an unfunctionalized EPDM copolymer. They also have tensile strengths and elongations which are comparable to or greater than those of the control employing an EPDM copolymer grafted with a substantially higher proportion of glycidyl methacrylate. From Table III, it is apparent that each of the compositions of this invention has a higher impact strength, and the products of Examples 14–17 a substantially higher impact strength, than those of the controls.

EXAMPLE 18

Following the procedure of Example 11, a similar blend was prepared in which the poly(butylene terephthalate) was replaced by a copolyester prepared from 1,4-butanediol and a 0.91:1 (by weight) mixture of dimethyl terephthalate and a dimide-diacid reaction product of trimellitic acid and a polyoxypropylenediamine having an average molecular weight of about 200. Said blend had a tensile strength of 10.5 MPa. and a tensile elongation of 435%. A control in which the ortho ester-grafted EPDM copolymer was replaced by an EPDM copolymer grafted with 3% glycidyl methacrylate had a tensile strength of 7.7 MPa. and a tensile elongation of 505%. Again, it is apparent that graft copolymers of the ortho esters of this invention may be employed at substantially lower levels of functionalization than corresponding glycidyl methacrylate graft copolymers, to obtain properties of the same order of magnitude.

I claim:

1. A cyclic ortho ester having the formula $$R^6CH=C-X-O+R^4\underset{p}{)}C-R^3 \diagup \overset{(CH_2)_n-O}{\underset{(CH_2)_m-O}{\diagdown}} C \diagup \overset{OR^1}{\underset{R^2}{\diagdown}} \quad (I)$$

wherein:
each of $R^1$ and $R^2$ is $C_{1-10}$ primary or secondary alkyl or a $C_{6-10}$ aralkyl or aromatic radical;
$R^3$ is hydrogen or $C_{1-4}$ primary or secondary alkyl;
$R^4$ is a $C_{1-6}$ alkylene or $C_{6-10}$ arylene radical;
$R^5$ is hydrogen or methyl;
Rhu 6 is hydrogen, $C_{1-6}$ alkyl or a $C_{6-10}$ aromatic radical;
X is $$-\overset{O}{\underset{\|}{C}}- \text{ or } -\!\!\!\bigcirc\!\!\!-CH_2-\ ;$$

m is 0 or 1;
n is from 1 to 2-m; and
p is 0 or 1.

2. A cyclic ortho ester according to claim 1 wherein m is 0 and n is 1.

3. A cyclic ortho ester according to claim 2 wherein $R^3$ and $R^6$ are each hydrogen.

4. A cyclic ortho ester according to claim 3 wherein p is 1.

5. A cyclic ortho ester according to claim 4 wherein $R^1$ is methyl.

6. A cyclic ortho ester according to claim 5 wherein $R^2$ is methyl or phenyl.

7. A cyclic ortho ester according to claim 6 wherein $R^4$ is methylene.

8. A cyclic ortho ester according to claim 7 wherein X is

   (II)

9. A cyclic ortho ester according to claim 8 wherein $R^2$ is methyl.

10. A cyclic ortho ester according to claim 8 wherein $R^2$ is phenyl.

11. A cyclic ortho ester according to claim 8 wherein $R^5$ is hydrogen.

12. A cyclic ortho ester according to claim 8 wherein $R^5$ is methyl.

13. A cyclic ortho ester according to claim 7 wherein X is

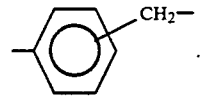   (III)

14. A cyclic ortho ester according to claim 13 wherein $R^2$ is methyl.

15. A cyclic ortho ester according to claim 13 wherein $R^2$ is phenyl.

16. A cyclic ortho ester according to claim 13 wherein $R^5$ is hydrogen.

17. 4-Acryloyloxymethyl-2-methoxy-2-methyl-1,3-dioxolane.

18. 4-Methacryloyloxymethyl-2-methoxy-2-methyl-1,3-dioxolane.

19. 4-Acryloyloxymethyl-2-methoxy-2-phenyl-1,3-dioxolane.

20. 4(2-Methoxy-2-methyl-1,3-dioxolanyl)methyl vinylbenzyl ether.

* * * * *